United States Patent [19]
Colon et al.

[11] Patent Number: 6,004,307
[45] Date of Patent: Dec. 21, 1999

[54] DIAPER PACKAGE

[76] Inventors: Ricardo Colon; Carmen R. Colon, both of 3015 N.W. 91$^{st}$. St., #104, Coral Springs, Fla. 33065

[21] Appl. No.: 09/094,952

[22] Filed: Jun. 15, 1998

[51] Int. Cl.$^6$ ...................................................... A61F 13/15
[52] U.S. Cl. ........................................ 604/385.1; 206/581
[58] Field of Search ........................ 604/385.1; 206/581, 206/223

[56] References Cited

U.S. PATENT DOCUMENTS

| | | |
|---|---|---|
| 4,011,945 | 3/1977 | Bourne et al. . |
| 4,553,665 | 11/1985 | Weick et al. . |
| 4,702,378 | 10/1987 | Finkel et al. ............................. 208/581 |
| 4,964,859 | 10/1990 | Feldman . |
| 5,065,868 | 11/1991 | Cornelissen et al. . |
| 5,261,531 | 11/1993 | Nieves . |
| 5,304,158 | 4/1994 | Webb ..................................... 604/385.1 |
| 5,413,568 | 5/1995 | Roach et al. . |
| 5,443,161 | 8/1995 | Jonese ..................................... 206/581 |
| 5,582,605 | 12/1996 | Lepie .................................... 604/385.1 |

*Primary Examiner*—John G. Weiss
*Assistant Examiner*—Catherine Cogut
*Attorney, Agent, or Firm*—Kenneth L Tolar

[57] ABSTRACT

An infant's diaper has an exterior surface to which a plurality of packets are adhesively secured each having a discrete hygienic item therein such as a pre-moistened towelette, ointments, powders and the like. The diaper is sealed within a water impermeable cover member having perforated side walls and a perforated top portion which may be separated allowing the cover to be spread and used as a diaper changing surface. The diapers may be prepackaged or transported in an accompanying carrying case.

7 Claims, 2 Drawing Sheets

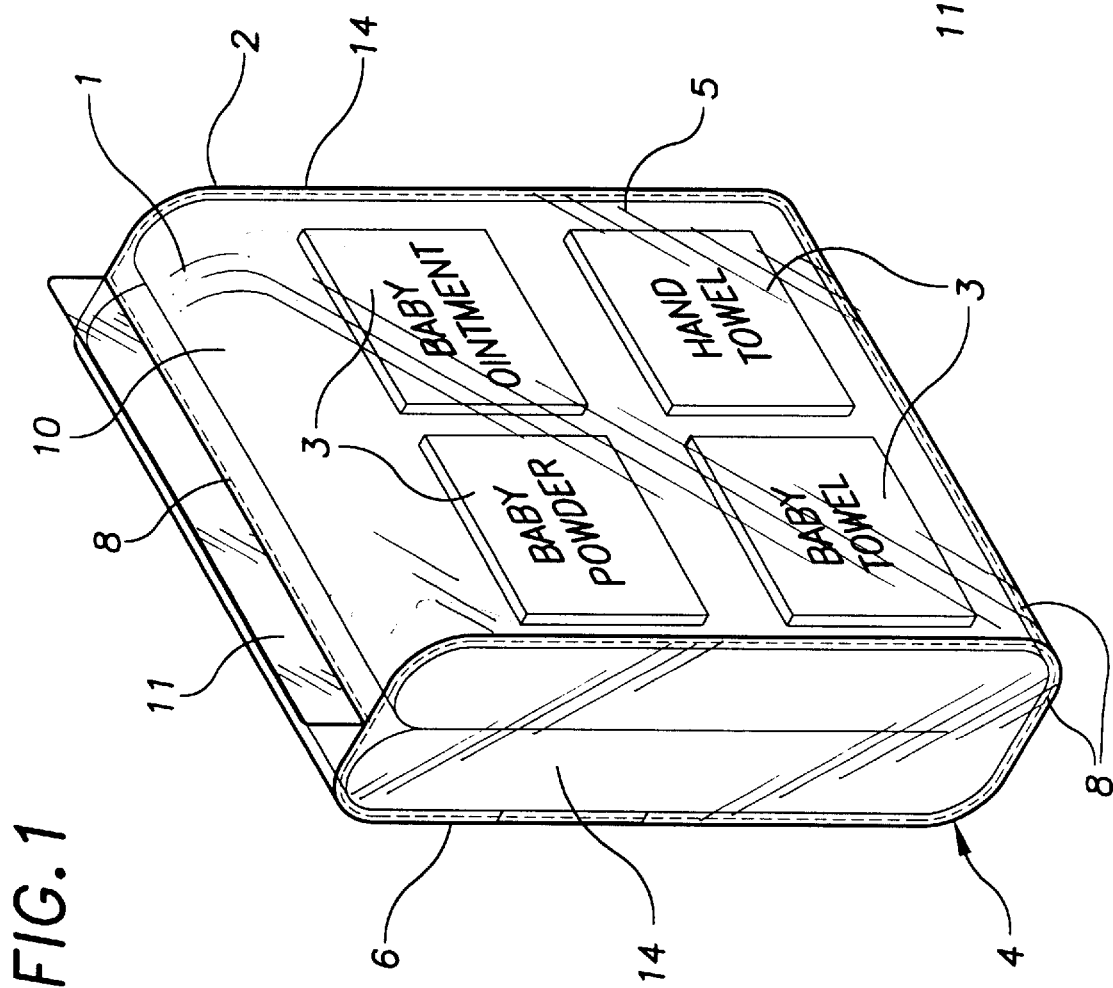

DIAPER PACKAGE

BACKGROUND OF THE INVENTION

The present invention relates to a diaper having a plurality of prepackaged hygienic items secured to the exterior thereof and which is sealed within a protective cover that may be separated and used as a diaper changing surface.

DESCRIPTION OF THE PRIOR ART

When changing an infant's diaper, numerous accessory items are often needed such as pre-moistened towelettes, baby powder, various ointments and similar items. These items are not always readily available especially when the parent and child are traveling or are otherwise away from home. Such items are typically stored in bulky containers that are difficult to transport or the parent may forget to pack such items altogether.

In addition, when changing a baby's diaper in a public place, a parent must often lay the child on a counter top, bench or similar surface which may be unsanitary. Changing a diaper on an exposed surface can also result in the surface being soiled unless a protective cover is placed thereover. Accordingly, there is currently a need for a disposable diaper that provides a user with convenient access to various hygienic items and a disposable protective changing surface.

Various diaper assemblies exist in the prior art. For example, U.S. Pat. No. 5,413,568 issued to Roach et al discloses a refastenable adhesive system for individually packaged, disposable absorbent articles. The device includes a foldable wrapper sealable with an adhesive strip for removably securing sanitary items therein.

U.S. Pat. No. 5,261,531 issued to Nieves discloses a feminine hygiene package including a dry wipe, an enclosed wet wipe, and a sanitary napkin all enclosed within a disposable container.

U.S. Pat. No. 5,065,868 issued to Cornelissen et al discloses a package consisting of an environmentally friendly paper bag for compactly packing compressed flexible articles therein.

U.S. Pat. No. 4,964,859 issued to Feldman discloses a diaper with integral changing pad/disposable container. The changing pad/disposable container is mounted to the outer surface of the diaper and includes a liquid impermeable membrane formed to define a closable pocket for retaining a towelette. The pocket is expandable to form a changing pad having an integral drawstring which may be pulled to a form disposable container.

U.S. Pat. No. 4,553,665 issued to Weick et al discloses a refillable case for freshen-up cloths.

U.S. Pat. No. 4,011,945 issued to Bourne et al discloses first aid equipment.

Although a diaper having a towelette and changing pad attached thereto is disclosed in Feldman, supra, the device does not include a plurality of distinct hygienic items according to the present invention. Furthermore, the towelette receptacle must be opened and the towelette removed in order for the changing mat to be used. The changing pad is heat sealed to the diaper thereby limiting the movement of the child and diaper relative to the changing pad. Accordingly, the diaper being removed must be disposed within the attached diaper changing mat after which the diaper changing mat is unavailable. It is usually more convenient to lay an infant onto a diaper changing protective surface, remove the soiled diaper, wipe the child and place the clean diaper thereon while the child remains on the protective diaper changing surface. Accordingly, the child never contacts the underlying counter top, bench, etc. Although it is suggested in Feldman, supra, that the changing mat be sold separately, it does not suggest a diaper sealed within a protective cover that may be removed and unfolded to form a surface that is independent of the diaper according to the present invention.

SUMMARY OF THE INVENTION

The present invention relates to a diaper having a plurality of hygienic items attached thereto that is sealed within a cover that is easily convertible to a diaper changing surface. The device includes a conventional diaper having a moisture absorbent inner layer, a moisture impermeable outer layer and one or more moisture absorbent layers therebetween. Adhesively secured to the exterior surface of the diaper are a plurality of sealed packets each having a discrete hygienic item therein such as ointment, baby powder, pre-moistened towelettes and petroleum jelly. The diaper is sealed within a plastic cover member having a pair of opposing perforated side walls and a top portion joined with a perforated strip allowing the cover member to be separated and laid flat to form a diaper changing surface. On the interior surface of the cover member are one or more pockets for receiving a soiled diaper or an expended packet. The diapers may be conveniently packaged or transported in an accompanying carrying case. It is therefore an object of the present invention to provide a diaper that eliminates the need to transport various hygienic items such as ointments, powders and towelettes therewith.

It is yet another object of the present invention to provide a diaper sealed within a protective cover which may be opened and used as a diaper changing surface.

It is yet another object of the present invention to provide a diaper sealed within a cover having a waste disposal pocket thereon. Other objects, features and advantages of the present invention will become readily apparent from the following detailed description of the preferred embodiment when considered with the attached drawings and the appended claims.

BRIEF DESCRIPTION OF THE DRAWINGS

FIG. 1 depicts the inventive device.

FIG. 2 is a side view of the inventive device.

DESCRIPTION OF THE PREFERRED EMBODIMENT

Figure 3:
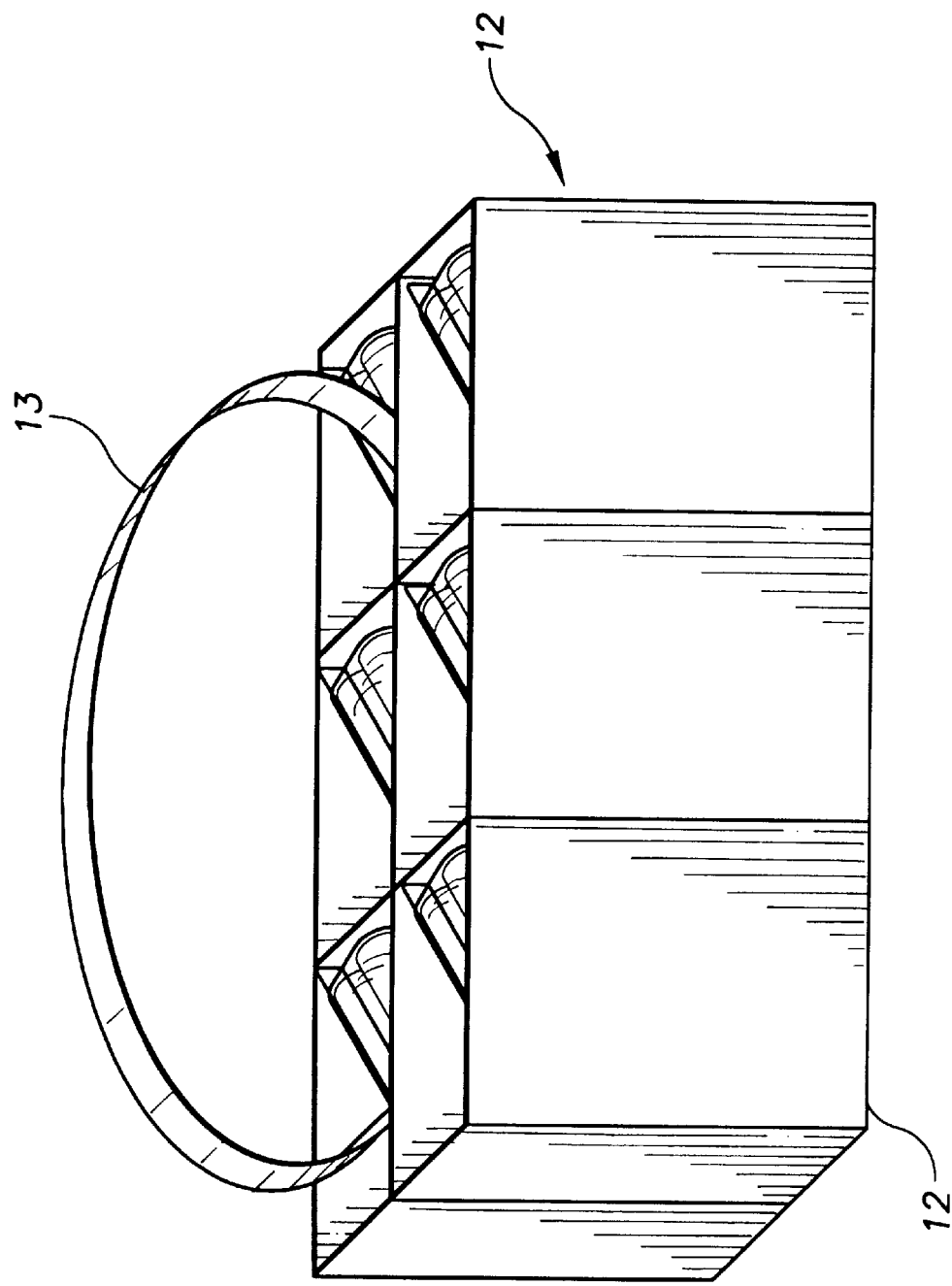
FIG. 3 depicts the accompanying carrying case according to the present invention.

Referring now to FIGS. 1 through 3, the present invention relates to a conventional diaper 1 having an inner layer made from a moisture absorbent material that contacts an infant's skin and an exterior surface 2 made from a water impermeable material with one or more layers of absorbent material therebetween. Attached to the exterior surface of the diaper are a plurality of packets 3 each containing a discrete hygienic item therein. In the preferred embodiment, each packet contains a sufficient amount of the hygienic item for a single application. As depicted in FIG. 1, the hygienic items may relate to a pre-moistened towelette, an ointment, a petroleum jelly and baby powder. However, as will be readily apparent to those skilled in the art, many other similar hygienic items may be used as well. Preferably the individual packets are adhesively secured to the exterior surface of the diaper although other conventional attachment means such as Velcro® may also be used.

Each diaper is sealed within a transparent, liquid impermeable cover member 4 made from plastic or a similar material having front 5, back 6, top 10 and two opposing side 14 portions. The front, back and side portions are joined with perforations 8. The top portion is separable with perforated strip 11 which may be removed to access a diaper therein. The side portions may then be separated from the front and rear portions and the cover may be laid flat to form a protective diaper changing surface. On the interior surface of the front or back portions of the cover member are one or more integral expandable pockets 15 dimensioned to receive a used diaper. Accordingly, after a child is laid on the changing surface and the soiled diaper is removed, the soiled diaper may be placed into one of the pockets and disposed simultaneously with the diaper changing surface.

A plurality of the diapers according to the present invention may be prepackaged or transported in an accompanying carrying case 12. As depicted in FIG. 3, the carrying case may include two side walls and two end walls therebetween and a bottom wall. One or more dividing walls extend from one side wall to the opposing side wall forming a plurality of segregated storage compartments each having an open top and dimensioned to receive at least one diaper package. The carrying case preferably has a strap 13 extending upwardly therefrom for assisting a user in carrying the device.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims.

What is claimed is:

1. A diaper package comprising:

a diaper member having an exterior surface;

a plurality of packets attached to the exterior surface of said diaper, each of said packets having a discrete hygienic item therein;

a water impermeable cover member sealably surrounding said diaper having perforated portions which may be separated to remove said diaper and which allows the cover member to be unfurled to form a protective diaper changing surface.

2. A diaper package according to claim 1 wherein the hygienic item is selected from the group consisting of baby powder, ointment, a pre-moistened towelette and a petroleum jelly.

3. A diaper package according to claim 1 wherein said cover member further includes an interior surface having a pocket thereon dimensioned to receive a diaper.

4. A diaper package according to claim 1 wherein said packets are adhesively secured to the exterior surface of said diaper.

5. A diaper package according to claim 1 further comprising an accompanying carrying case having a plurality of segregated compartments each having an open top through which a diaper may be inserted, each of said compartments dimensioned to receive at least one of said diapers, said case having a strap which may be grasped by a user.

6. A diaper package according to claim 1 wherein said cover member is constructed with a transparent material.

7. A diaper package according to claim 1 wherein said packets are secured to the exterior surface of said diaper using a hook and loop fastener.

* * * * *